United States Patent [19]

Wallquist et al.

[11] Patent Number: 5,238,984

[45] Date of Patent: Aug. 24, 1993

[54] DIANTHRAQUINONYL COMPOUNDS

[75] Inventors: Olof Wallquist, Marly; Guy de Weck, Basel; Gary Wooden, Oberschrot, all of Switzerland

[73] Assignee: Ciba-Geigy Corporation, Ardsley, N.Y.

[21] Appl. No.: 715,034

[22] Filed: Jun. 11, 1991

Related U.S. Application Data

[63] Continuation of Ser. No. 594,877, Oct. 9, 1990, abandoned.

[30] Foreign Application Priority Data

Oct. 10, 1989 [CH]  Switzerland ................... 3693/89

[51] Int. Cl.$^5$ .......................... C08K 5/20; C09B 1/40; C09B 1/42
[52] U.S. Cl. ................................ 524/218; 552/212
[58] Field of Search ............................ 524/218

[56] References Cited

U.S. PATENT DOCUMENTS

| | | | |
|---|---|---|---|
| 3,723,479 | 3/1973 | Schuhmacher | 552/212 |
| 3,945,955 | 3/1976 | Ihde, Jr. | 521/75 |

FOREIGN PATENT DOCUMENTS

| | | | |
|---|---|---|---|
| 2250107 | 4/1973 | Fed. Rep. of Germany | 552/212 |
| 2200115 | 7/1973 | Fed. Rep. of Germany . | |
| 49-1289 | 1/1974 | Japan | 552/212 |
| 49-3346 | 1/1974 | Japan . | |
| 984110 | 2/1965 | United Kingdom . | |
| 1346126 | 2/1974 | United Kingdom . | |

Primary Examiner—Joseph L. Schofer
Assistant Examiner—Wu C. Cheng
Attorney, Agent, or Firm—JoAnn Villamizar; George R. Dohmann

[57] ABSTRACT

Dianthraquinonyl compounds of formula

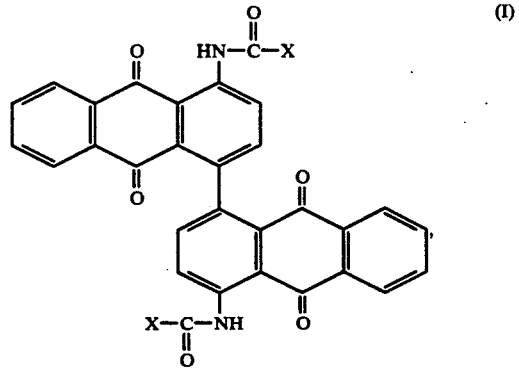

wherein
X is a radical $R_1$, $R_2$, $R_3$ or $R_4$, and
$R_1$ is alkyl or alkenyl of not less than 8 carbon atoms,
$R_2$ is —$OR_1$ or —$SR_1$,
$R_3$ is —$NHR_1$ or —$N(R_1)_2$, and
$R_4$ is a group of formula

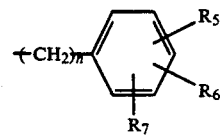

wherein
$R_5$ is —$NHR_1$, —$N(R_1)_2$, —$OR_1$ or —$SR_1$ and n is 0, 1 or 2, and
$R_6$ and $R_7$ are each independently of the other hydrogen, halogen, nitro, $C_1$-$C_4$alkyl or $C_1$-$C_4$alkoxy.

These dianthraquinonyl compounds are preeminently suitable for the mass coloration of plastics materials, especially of polyolefins.

6 Claims, No Drawings

DIANTHRAQUINONYL COMPOUNDS

This application is a continuation of application Ser. No. 594,877, filed Oct. 9, 1990, now abandoned.

The present invention relates to dianthraquinonyl compounds containing specific carbonylamino groups which carry higher alkyl radicals and to the use thereof for the mass coloration of plastics materials, especially of polyolefins.

Dianthraquinonyl compounds containing lower acylamino groups or benzoylamino groups which may be substituted by lower alkyl groups and the use thereof for pigmenting coating compositions, synthetic resins, synthetic fibers, printing inks, rubber and the like, are disclosed in Japanese patent 743,346. Although these compounds have good allround fastness properties, they do not meet in all respects the current stringent requirements of technology for certain applications.

It has now been found that a surprising enhancement of the pigment properties, especially dispersibility as well as fastness to light, weathering and heat, can be achieved by introducing higher alkyl radicals into such dianthraquinonyl compounds.

Accordingly, the present invention relates to dianthraquinonyl compounds of formula

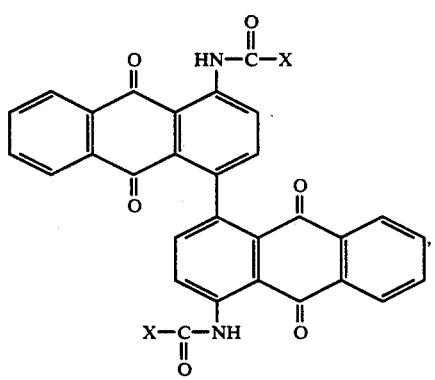

(I)

wherein
X is a radical $R_1$, $R_2$, $R_3$ or $R_4$, and
$R_1$ is alkyl or alkenyl of not less than 8 carbon atoms,
$R_2$ is $-OR_1$ or $-SR_1$,
$R_3$ is $-NHR_1$ or $-N(R_1)_2$, and
$R_4$ is a group of formula

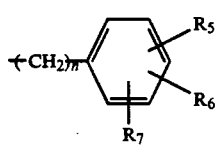

wherein
$R_5$ is $-NHR_1$, $-N(R_1)_2$, $-OR_1$ or $-SR_1$ and n is 0, 1 or 2, and
$R_6$ and $R_7$ are each independently of the other hydrogen, halogen, nitro, $C_1$–$C_4$alkyl or $C_1$–$C_4$alkoxy.

$R_1$ as alkyl of not less than 8 carbon atoms is branched or straight-chain alkyl such as n-octyl, n-nonyl, n-decyl, n-dodecyl, n-tridecyl, isotridecyl, n-tetradecyl (myristyl), n-pentadecyl, n-hexadecyl, 1-methylpentadecyl, n-octadecyl, n-eicosyl, n-tetracosyl, n-hexacosyl, n-triacontyl and n-pentacontyl.

$R_1$ as alkenyl of at least 8 carbon atoms is branched or straight-chain alkenyl such as 8-heptadecenyl or 9-decenyl.

$R_1$ is preferably $C_{10}$–$C_{35}$alkyl, most preferably $C_{12}$–$C_{18}$alkyl, or mixtures thereof, and is derived, for example, from long-chain alkanols such as n-decyl alcohol, lauryl alcohol, myristyl alcohol, cetyl alcohol and stearyl alcohol, as well as from the unbranched primary alcohols which always contain an even number of carbon atoms (the alkyl groups are here designated as "alfyl", for example $C_{12}$alfyl, $C_{14}$alfyl) and which are obtainable as ®Alfols (sold by Condea).

Particularly preferred dianthraquinonyl compounds of formula I are those wherein X is $C_{12}$–$C_{18}$alkyl or a group of formula

wherein $R_5$ is $-NHR_1$, $-N(R_1)_2$, $-OR_1$ or $-SR_1$ and $R_1$ is $C_{12}$–$C_{18}$alkyl, and, most especially, those wherein X is straight-chain $C_{12}$–$C_{18}$alkyl.

The compounds of formula I can be prepared by processes analogous to known ones, for example starting from 1 mol of the compound of formula

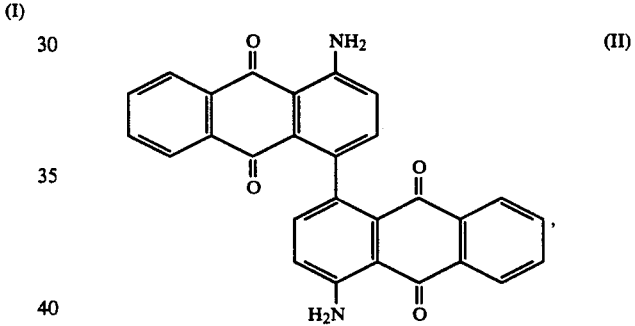

(II)

a) when X is $R_1$, $OR_1$, $SR_1$, $N(R_1)_2$ or $R_4$, by condensation with 2 mol of a compound of formula

(III)

b) when X is NH—$R_1$, by addition of 2 mol of a compound of formula

(IV)

and, c) when X is $OR_1$, $SR_1$, $NHR_1$ or $N(R_1)_2$, by condensation with 2 mol of phosgene to the diisocyanate and subsequent addition of 2 mol of an alcohol of formula

(V), of an amine of formulae

(VI), or

(VII), or of a mercaptan of formula

HSR₁  (VIII), wherein Y in formula III is halogen, for example bromo or, preferably, chloro, and R₁ in formulae IV to VIII has the meanings given above.

The compounds II to VIII are known. However, should any be novel, they can be prepared by methods which are known per se.

The condensation and addition reactions of a), b) and c) are conveniently carried out in the presence of an organic inert solvent under normal or elevated pressure, with or without a catalyst. Suitable solvents are, typically, toluene, xylene, chlorobenzene, dichlorobenzenes such as o-dichlorobenzene, and also trichlorobenzenes, nitrobenzene, or mixtures of aromatic and/or aliphatic solvents such as ®Shellsols.

The compounds of formula I are isolated after their synthesis in conventional manner, for example by filtration. The filter product is washed, for example, with one of the above mentioned solvents and then conveniently with water. They are obtained in good yield and purity and can in principle be used, even without further purification, in finely particulate form for the mass coloration of plastics materials, especially of polyolefins.

If the compounds of this invention are still not of optimum or sufficient purity and/or particle form and size for use as pigments, they can be further conditioned. By conditioning is meant the preparation of a fine particle size and form best suited to the application, for example by dry milling with or without salt, by solvent or aqueous milling or by salt-kneading, or by a subsequent hot solvent treatment.

Hot solvent treatments can be carried out, for example, in organic solvents, preferably those which have a boiling point above 100° C.

Particularly suitable solvents for this aftertreatment are halobenzenes, alkylbenzenes or nitrobenzenes, for example toluene, chlorobenzene, o-dichlorobenzene, xylenes or nitrobenzene; alcohols such as isopropanol or isobutanol; and also ketones such as cyclohexanone; ethers such as ethylene glycol monomethyl or monoethyl ether; amides such as dimethyl formamide or N-methylpyrrolidone; as well as dimethyl sulfoxide, sulfolane or water by itself, under normal or elevated pressure. The aftertreatment can also be carried out in water in the presence of organic solvents and/or with the addition of surface-active substances or aliphatic amines, or in liquid ammonia.

Depending on the conditioning method and/or end use, it may be convenient to add specific amounts of texture improvers to the compounds of formula I before or after the conditioning. Preferred texture improvers are, typically, fatty acids containing not less than 18 carbon atoms, for example stearic acid or behenic acid or the amides or metal salts thereof, preferably magnesium salts. The texture improvers are preferably added in amounts of 0.1–30% by weight, most preferably of 2–15% by weight, based on the final product.

Owing to their excellent compatibility with polyolefins, the compounds of formula I obtained in this invention can often be used for colouring polyolefins by direct incorporation therein without further conditioning.

Although the compounds of formula I are especially suitable for the mass coloration of polyolefins, they can also be used advantageously for colouring other polymers, for example polyvinyl chloride, fluorinated polymers such as polyfluorethylene, polytrifluorochloroethylene or tetrafluoroethylene/hexafluoropropylene copolymer, but preferably for engineering plastics such as polycarbonates, polyacrylates, polymethacrylates, ABS, polyesters, polyamides, polyether ketones, polyurethanes, singly or in mixtures. They are conveniently used in a concentration of 0.01 to 5% by weight, based on the polymer.

Exemplary of polyolefins which can be coloured with the compounds of formula I are high and low density polyethylene (HD-PE, LD-PE and LLD-PE), polypropylene and polyisobutylene, and also copolymers of polyolefins with, for example, polyethers, polyether ketones or polyurethanes. Polypropylene is preferred.

Coloration is effected by conventional methods, for example by blending a compound of formula I, or with a mixture of such compounds, with the plastics material in granular or powder form without first having to incorporate it in a preparation, and then extruding the blend to fibres, sheets or granular formulations. These last mentioned formulations can then be shaped to objects by injection moulding.

The colorations obtained are of great clarity and excellent saturation and have good transparency as well as good fastness properties, especially fastness to heat and light. A particular advantage of the polyethylene objects coloured with the compounds of formula I is that-especially in the case of high density polyethylene-they exhibit no increased tendency to deformation.

The fibres, especially the polypropylene fibres, coloured with the compounds of formula I are brilliant and have excellent textile properties such as lightfastness and fastness to washing and solvents. The use of compounds of formula I is also associated with a number of technical advantages, for example very easy dispersibility, few fibre ruptures, insignificant clogging of the spinnerets, and reduced filtration times.

The invention is illustrated by the following Examples.

EXAMPLE 1

14.6 g of stearoyl chloride are added dropwise to a suspension of 7.1 g of 1,1'-diamino-4,4'-dianthraquinone in 150 ml of chlorobenzene. The suspension is heated to 125° C., stirred at this temperature for 18 hours, allowed to cool, and filtered. The filter cake is washed with methanol. For purification, the moist colorant is boiled in methanol for 2 hours. After filtration, the filter cake is washed once more with methanol and dried in a vacuum shelf drier to give 15.0 g of the compound of formula

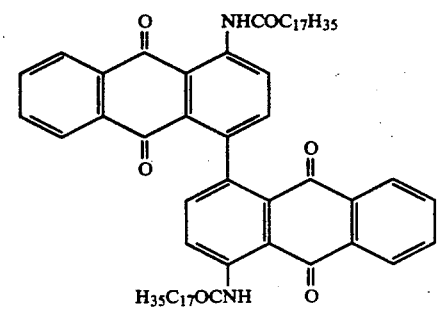

as a greenish yellow powder.

| Analysis for $C_{64}H_{84}N_2O_6$ | | | |
|---|---|---|---|
| | C | H | N |
| cal.: | 78.65 | 8.66 | 2.87 |
| found: | 78.58 | 8.43 | 2.70 |

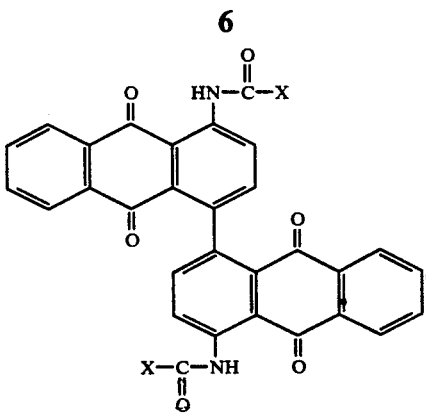

(I)

EXAMPLES 2 AND 3

The procedure of Example 1 is repeated, except that the equivalent amount of an acid chloride of formula XCOCl, wherein X has the meanings given in the table, is used in place of stearoyl chloride, to give corresponding compounds of formula I.

| Example | X | Yield | Colour | | Analysis (%) | | | |
|---|---|---|---|---|---|---|---|---|
| | | | | | C | H | N | Cl |
| 2 | $C_{11}H_{23}-$ | 65% | yellow | cal.: | 77.2 | 7.5 | 3.5 | — |
| | | | | found: | 77.2 | 7.5 | 3.4 | — |
| 3 | $C_7H_{15}CH=CH-(CH_2)_7-$ | 63% | yellow | cal.: | 77.0 | 11.6 | 2.0 | — |
| | | | | found: | 77.3 | 11.7 | 2.2 | — |
| 4 | $C_{15}H_{31}-$ | 59% | yellow | cal.: | 78.4 | 8.1 | 3.1 | — |
| | | | | found: | 78.0 | 8.3 | 2.7 | — |
| 5 | 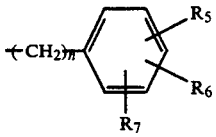 | 89% | yellow | cal.: | 78.8 | 8.1 | 2.4 | — |
| | | | | found: | 78.8 | 8.1 | 2.4 | — |
| 6 | 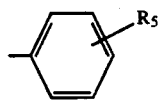 | 87% | yellow | cal.: | 74.4 | 7.5 | 2.2 | 5.6 |
| | | | | found: | 74.2 | 7.7 | 2.1 | 5.7 |

EXAMPLE 7

A mixture of 1.0 g of the pigment obtained in Example 1, 1.0 g of antioxidant (®IRGANOX 1010, Ciba-Geigy AG) and 1000 g of high density polyethylene granules (®VESTOLEN A 60-16, HÜLS) is stirred for 15 minutes in a glass flask on a roller gear table. The mixture is then extruded in two passes in a single screw extruder. The granulate so obtained is moulded to plates at 220° C. in an injection moulding machine (Allround Aarburg 200) and then post-formed for 5 minutes at 180° C. The mouldings are coloured in strong yellow shades of excellent fastness properties.

EXAMPLE 8

0.6 g of the pigment obtained in Example 1 are mixed with 67 g of polyvinyl chloride, 33 g of dioctyl phthalate, 2 g of dibutyltin laurate and 2 g of titanium dioxide and the mixture is processed to a thin sheet on a roll mill for 15 minutes at 160° C. The PVC sheet so obtained is coloured in a very strong yellow shade which is fast to light.

EXAMPLE 9

1000 g of polypropylene granules (®DAPLEN PT-55, ex Chemie Linz) and 4 g of the pigment obtained in Example 1 are thoroughly mixed in a mixing drum. The granules so obtained are melt spun at 260°–285° C. to yellow filaments of very good textile fibre properties such as light- and wetfastness.

What is claimed is:

1. A plastic material mass colored with a dianthraquinonyl compound of the formula I wherein X is a radical $R_1$ or $R_4$ and $R_1$ is $C_{10}$–$C_{35}$alkyl, 8-heptadecenyl or 9-decenyl and $R_4$ is a group of formula wherein
$R_5$ is $-NHR_1$, $-N(R_1)_2$, $-OR_1$ or $-SR_1$ and n is 0, 1 or 2, and
$R_6$ and $R_7$ are each independently of the other hydrogen, halogen, nitro, $C_1$–$C_4$alkyl or $C_1$–$C_4$alkoxy.

2. A plastics material according to claim 1 which is a polyolefin.

3. A plastics material according to claim 1 which is polypropylene.

4. A plastic material according to claim 1 wherein $R_1$ is $C_{12}$–$C_{18}$alkyl.

5. A plastic material according to claim 1, wherein X is $C_{12}$–$C_{18}$alkyl or a group of the formula wherein $R_5$ is $NHR_1$, $-N(R_1)_2$, $-OR_1$ or $-SR_1$ and $R_1$ is $C_{12}$–$C_{18}$alkyl.

6. A plastic material according to claim 1 wherein X is a straight-chain $C_{12}$–$C_{18}$alkyl.

* * * * *